United States Patent
Lykke et al.

(10) Patent No.: US 8,710,130 B2
(45) Date of Patent: Apr. 29, 2014

(54) PERMEABLE PRESSURE SENSITIVE ADHESIVE

(75) Inventors: Mads Lykke, Broenshoej (DK); Astrid Toftkaer, Soeborg (DK); Hasse Buus, Humlebaek (DK); Tom Kongebo, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 431 days.

(21) Appl. No.: 12/452,513

(22) PCT Filed: Jun. 17, 2008

(86) PCT No.: PCT/DK2008/050146
§ 371 (c)(1),
(2), (4) Date: Apr. 26, 2010

(87) PCT Pub. No.: WO2009/006901
PCT Pub. Date: Jan. 15, 2009

(65) Prior Publication Data
US 2010/0204632 A1  Aug. 12, 2010

(30) Foreign Application Priority Data
Jul. 6, 2007  (DK) ................................ 2007 01003

(51) Int. Cl.
*A61F 13/02* (2006.01)
*C09J 123/08* (2006.01)

(52) U.S. Cl.
USPC ........... 524/284; 524/582; 524/563; 524/556; 524/424; 524/428

(58) Field of Classification Search
USPC .......... 524/582, 563, 556, 270, 284, 424, 428
See application file for complete search history.

(56) References Cited

U.S. PATENT DOCUMENTS

| | | | |
|---|---|---|---|
| 3,615,106 A | 10/1971 | Flanagan et al. | |
| 4,191,673 A | 3/1980 | Wiesman | |
| 4,477,325 A | 10/1984 | Osburn | |
| 4,551,490 A | 11/1985 | Doyle et al. | |
| 5,054,488 A | 10/1991 | Muz | |
| 5,086,764 A | 2/1992 | Gilman | |
| 5,133,821 A | 7/1992 | Jensen | |
| 5,257,491 A * | 11/1993 | Rouyer et al. | 53/428 |
| 5,458,124 A | 10/1995 | Stanko et al. | |
| 6,084,010 A * | 7/2000 | Baetzold et al. | 523/210 |
| 6,180,544 B1 | 1/2001 | Jauchen et al. | |
| 6,225,520 B1 | 5/2001 | Bauduin et al. | |
| 6,372,951 B1 | 4/2002 | Ter-Ovanesyan et al. | |
| 6,385,473 B1 | 5/2002 | Haines et al. | |
| 6,559,351 B1 * | 5/2003 | Eakin | 602/56 |
| 6,933,342 B2 | 8/2005 | Parg et al. | |
| 2003/0009097 A1 | 1/2003 | Sheraton et al. | |
| 2006/0106167 A1 * | 5/2006 | Shah | 525/123 |
| 2006/0264549 A1 * | 11/2006 | Rolland | 524/425 |
| 2007/0254131 A1 * | 11/2007 | Shail et al. | 428/95 |

FOREIGN PATENT DOCUMENTS

| | | |
|---|---|---|
| CN | 1188129 A | 7/1998 |
| CN | 1351104 A | 5/2002 |
| EP | 0 019 926 A1 | 12/1980 |
| EP | 0 236 104 A2 | 9/1987 |
| EP | 0 264 299 A2 | 4/1988 |
| EP | 0 641 553 A1 | 3/1995 |
| WO | WO 91/01706 | 2/1991 |
| WO | WO 99/11302 | 3/1999 |
| WO | WO 99/59465 | 11/1999 |
| WO | WO 02/05737 A1 | 1/2002 |
| WO | WO 02/066087 A1 | 8/2002 |
| WO | WO 03/065926 A2 | 8/2003 |

* cited by examiner

*Primary Examiner* — Robert D. Harlan
(74) *Attorney, Agent, or Firm* — Coloplast Corp., Coloplast A/S; Nick Baumann

(57) ABSTRACT

The present invention relates to a pressure sensitive, hot melt processable adhesive composition comprising a polar plasticising oil and a polar polyethylene copolymer, and a layered adhesive construct and a medical device comprising the adhesive composition according to the invention.

32 Claims, No Drawings

PERMEABLE PRESSURE SENSITIVE ADHESIVE

This is a national stage of PCT/DK08/050146 filed Jun. 17, 2008 and published in English, which has a priority of Denmark no. PA 2007 01003 filed Jul. 6, 2007, hereby incorporated by reference.

FIELD OF THE INVENTION

The present invention relates to a pressure sensitive, hot melt processable adhesive composition comprising polar plasticising oil and a polar polyethylene copolymer, and a layered adhesive construction and a medical device comprising the adhesive composition according to the invention.

BACKGROUND OF THE INVENTION

Pressure sensitive adhesives have for a long time been used for attaching medical devices, such as ostomy appliances, dressings (including wound dressings), wound drainage bandages, devices for collecting urine, orthoses and prostheses to the skin.

Hydrocolloid adhesives containing hydrophilic particles or absorbents, which absorb moisture into the adhesive bulk and transmit moisture when conditions are saturated, are one well-known group of pressure sensitive adhesives useful for attaching medical devices to the skin. However, the retention of moisture in hydrocolloid adhesives may cause changes in the adhesive, such as swelling, loss of cohesion and disintegration. Non-absorbing adhesives on the other hand, may trap excessive moisture between the skin and adhesive, causing weakening of adhesion and maceration of the skin.

Due to the delicate nature of skin, there is a narrow window where a pressure sensitive adhesive can function as a good and skin friendly adhesive: On one hand, the adhesive should be able to attach the medical device to the skin and the device should not fall of during wear and on the other hand, removal of the medical device from the skin should not cause damage to the skin.

For medical uses, a high water vapour transmission through the pressure sensitive adhesive is desirable. However, the availability of pressure sensitive adhesives with high water vapour transmission, which are suitable for skin contact use, is limited.

The water vapour transmitting pressure sensitive adhesives currently used for adhesion to the skin are mainly silicone, PU and acrylic based adhesives.

Pressure sensitive adhesives based on acrylics are usually solvent based and may include toxic residues and monomers causing malodour. These adhesives may incorporate hydrophilic components, such as hydrocolloids, which absorb moisture. However, the content of hydrophilic components and hence the absorption of moisture changes the properties of the adhesive, swelling and reduced adhesion being the most undesirable effects. The wear time of such acrylic adhesives is typically short due to these effects.

Silicone adhesives are relatively expensive and have a relatively low moisture transmission, which causes problems with regard to breathability. Adhesion may also be compromised, when moisture builds up between the skin and the adhesive. Moreover, the compatibility of silicones with other organic materials (e.g. polymers) is limited, which affects the blending stability with performance enhancing additives, and adhesion to reinforcement materials of another chemical composition.

Pressure sensitive adhesives based on silicone or polyurethane are typically thermoset materials that undergo an irreversible cross-linking reaction during processing.

Adhesives based on apolar polymers like SIS and PIB are well known in the technical field of medical adhesives. E.g. WO 99/11302 describing adhesives for medical use based on SIS, PIB and hydrocolloids and U.S. Pat. No. 4,551,490 describing adhesives containing SIS/SI, PIB/butyl rubber, tackifier, mineral oil and hydrocolloids.

Ethylene copolymers are often used in hot-melt adhesives for e.g. packaging and labels. The EVAs used for these purposes are the traditional EVA types containing up to 40% vinyl acetate, i.e. the polymer is relatively apolar.

Adhesives containing EVA with more than 40% vinyl acetate are also described.

U.S. Pat. No. 4,477,325 describes a skin barrier composition made of EVA, PIB and water absorbing particles or polymers. The EVA may contain from 25 to 65% by weight of vinyl acetate.

U.S. Pat. No. 6,933,342 describes a formulation comprising a triblock copolymer (styrene-diene-styrene), a terpene resin, a liquid and EVA polymer wherein the EVA polymer preferably possess a vinyl acetate content of more than 50% by weight.

U.S. Pat. No. 6,225,520 describes an adhesive containing ethylene copolymer as e.g. EVA, solid tackifier resin, liquid tackifier resin, antioxidant and optionally a diluent. The EVA polymer exhibiting a vinyl acetate content of between 15 and 65% by weight. The invention relates to adhesives for labels and tapes, including tapes for skin contact.

The adhesive described above all have the drawback that they contain apolar components, which result in an adhesive matrix (adhesive without hydrocolloids) with no or low water permeability. If the adhesive has to be used for skin contact, they need to be able to handle moisture. When the types of materials described above are used as skin adhesives, a large amount of absorbing particles are often added to handle the moisture.

The addition of particles in large amounts results in a relatively hard adhesive material, which has reduced tack and weak durability and often leads to skin stripping. To avoid this kind of skin damage, it can be an advantage to use a permeable adhesive material that can handle the moisture developed at the skin surface. Hereby no or a low amount of hydrocolloids needs to be added.

It has been found that pressure sensitive adhesives based on polar ethylene copolymers and polar oil or a combination of polar oils provides an excellent skin adhesive.

These adhesives also have a very high moisture vapour transmission rate, which makes them breathable and very skin friendly. The high moisture transmission of these adhesives is a particular advantage where a medical device has to be worn on the skin for a long time, e.g. days.

It has surprisingly been found, that the adhesives according to the invention provide softness, flexibility, safety and comfort in wear, a low toxicity compared with acrylic adhesives and a good moisture transmission compared to silicon adhesives.

SUMMARY OF THE INVENTION

Polymers that may be used in the practice of the invention will generally be copolymers of ethylene and a polar monomer. The copolymers typically comprise less than about 70% ethylene, have water vapour transmission of more than 50 $g/m^2$/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapour transmission of more than 50 g/m$^2$/day for a 150 μm sheet when measured according to MVTR Test Method.

Polar oils, which may be used in the invention, will generally be those that have good solubility in the polar domains of the polymer, i.e. provide softness without sacrificing too much tensile strength of the polymer. Oils that can support good water vapour permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene.

DETAILED DESCRIPTION OF THE INVENTION

It has now been discovered that hot melt adhesives with aggressive tack and peel as well as good water vapour permeability can be obtained in using polar ethylene copolymers, when the polymer with a low melt flow index is formulated with a suitable polar oil and optionally other ingredients.

The adhesives of the invention exhibit unique features that make them useful for a variety of applications. Features such as good adhesion to skin, high water vapour transmission rate and resistance to radiation sterilisation. These features make the adhesives of the invention well suited adhesives for many applications and particularly well suited for medical applications such as faecal management devices, wound care appliances, and incontinence devices.

The breathable adhesives of the invention may be used for fixation applications, e.g. as adhesives for medical tapes, band aids and fixation of pads, foams or needles, providing good adhesion, high breathability and sterilisation tolerance.

Adhesives of the invention may be formulated as traditional hydrocolloid containing adhesives providing improved moisture handling properties and improved sterilisation tolerance.

The high moisture vapour transmission rate of the adhesives of the invention makes them very suitable for laminated device constructions with more than one adhesive layer. In example devices, where a non-absorbing substrate contact layer is combined with an absorbing bulk adhesive layer combining tack and durability with good absorption.

In one embodiment of the present invention, a pressure sensitive, hot melt processable adhesive composition comprising a polar plasticising oil or a combination of polar plasticising oils in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10 min (190° C./21.1N).

In one embodiment of the present invention, a pressure sensitive, hot melt processable adhesive composition is produced by mixing a polar plasticising oil or a combination of polar plasticising oils in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10 min (190° C./21.1N).

In an embodiment of the invention, the final adhesive in continuous form exhibiting moisture vapour transmission rate of at least 100 g/m$^2$/day for a 150 μm adhesive sheet when measured according to MVTR Test Method.

The primary polymers used in the adhesive composition are ethylene copolymers. The copolymer should contain a considerable amount of a polar component to get high water permeability. Preferably, the ethylene parts of the copolymer can form crystalline areas that ensure the cohesive strength of the adhesive.

In one embodiment of the invention, the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

The polar polyethylene copolymer is preferably ethylene vinyl acetate.

By polar polymers is meant polymers with water transmission above 50 g/m$^2$/day for a 150 μm film when measured according to MVTR Test Method.

One object of this invention is to provide water permeable adhesive that is an adhesive, which can be hot-melt processed and which at normal use conditions can be removed without leaving significant residues.

In an embodiment of the invention the ethylene vinyl acetate has a content of at least 40% (w/w) vinyl acetate preferably with 40-80% (w/w) vinyl acetate.

The adhesive composition should fulfill the Dahlquist's criterion. Preferably, the modulus should be below 100 000 Pa, and for very soft, skin friendly and comfortable adhesive the modulus (G') could be as low as 1-30 kPa measured by DMA at 32° C. and 1 Hz.

It is of great importance, that the adhesive is as soft as possible to ensure a skin friendly material that is comfortable to wear. To get a soft material, the polymer content should be as low as possible. The maximum polymer content of the polar polyethylene copolymer should not exceed 50% (w/w) of the final adhesive.

Preferably, the polar polyethylene copolymers used in the adhesive should have a molecular structure at a level that results in a melt flow index (MFI) below 2 g/10 min (190° C./21.1N). The melt flow index can be measured by the methods given in ISO 1133 and ASTM D1238.

The advantage of using a polymer with high molecular weight and low MFI is that the high molecular weight polymer can ensure a sufficient high cohesive strength to the adhesive.

By the content of the final adhesive is meant the percentage in weight of the ingredient in relation to the total weight of the ingredients used in the adhesive composition.

In an embodiment of the invention, the content of the polar polyethylene copolymer is 10-45% (w/w) of the final adhesive preferably 15-30%.

In another embodiment of the invention, the polar polyethylene copolymer has a molecular weight above 250000 g/mol.

In one embodiment of the present invention, the adhesive composition comprising a polar plasticising oil or a combination of polar plasticising oils in the content of 20-70% (w/w) of the final adhesive preferably 40-65%.

Polar oils, which may be used in the invention, will generally be those that have good solubility in the polar domains of the polymer, i.e. provide softness without sacrificing too much tensile strength of the polymer. Oils that can support good water vapour permeability are preferred, a 50:50 mix of polymer and oil should have a moisture vapour transmission rate of at least 100 g/m$^2$/day. Examples of such oils are vegetable and animal oils and derivatives thereof. Preferred polar oils are esters, ethers and glycols and particularly preferred is Poly Propylene Oxide, e.g. alpha-butoxy-polyoxypropylene.

The adhesive should preferable contain about or more than 50% plasticising oil to get the optimal softness and skin friendliness.

In one embodiment of the present invention, the adhesive composition comprising a polar plasticising oil wherein the polar plasticising oil is selected from the group of liquid rosin derivatives, aromatic olefin oligomers, vegetable and animal oils and derivatives, preferable polar oils are esters, ethers and glycols and particularly preferred is poly propylene oxides such as alpha-butoxy-polyoxypropylene.

Furthermore, polypropylene oxide oil contributes to a high permeability of the adhesive composition.

Some of the adhesive compositions according to the invention contain a minor amount of additional polymer besides the main polymer giving cohesion. This or these additional polymers are added to give tack. These additional polymers are optional and not necessary for all purposes.

In one embodiment of the invention, the adhesive composition further comprises a low molecular weight polymer, i.e. MFI>2.

The addition of a low Mw polymer to the adhesive may be an advantage when a lot of moist is present between the adhesive and the skin.

Preferably the total polymer content, including polar polyethylene copolymer and additional polymers (not including oils, tackifier resin etc), should not exceed 50% (w/w) of the final adhesive.

Additional components may be added to the composition such as tackifier resin, plasticisers and wax.

In one embodiment of the invention, the adhesive composition further comprises a tackifying resin such as natural, modified or synthetic resins preferably polar resins such as rosins, rosin esters, hydrogenated rosins, hydrogenated rosin esters, and derivatives of such polar resins or pure aromatic monomer resins.

Tackifying resins can be added to control tack in the adhesives, i.e. reduce moduli and increase glass transition temperature.

The content of the tackifying resin is 0-40% (w/w) of the final adhesive. Preferably the adhesive is substantially free of resin. When the adhesive composition is containing resin the content of the tackifying resin is preferably 0.1-40% (w/w) of the final adhesive and more preferably 10-20% (w/w) of the final adhesive.

In one embodiment of the present invention, the adhesive composition comprising polar plasticising oils and resin in the content of above 50% (w/w) of the final adhesive.

In one embodiment of the invention, the adhesive composition further comprises an additional plasticiser selected from the group of mineral oil, citrate oil, paraffin oil, phatalic acid esters, adepic acid esters (e.g. DOA), and liquid or solid resin.

In another embodiment of the invention, the adhesive composition further comprises a polyethylene wax.

Other ingredients may be added for auxiliary benefits. This could be antioxidants and stabilisers, fillers for rheology modification or active components like vitamin E or ibuprofen.

In another embodiment of the invention, the adhesive composition further comprises other ingredients selected from the group of antioxidants, stabilisers, fillers, pigments, flow modifiers, and active ingredients.

In one preferred embodiment of the invention, the adhesive composition comprises polar active ingredients.

The adhesive composition according to the invention is tolerant for beta sterilisation, which means that it does not significantly degrade or change properties during beta sterilisation at a reasonable level.

In one embodiment of the invention, a beta-sterilised adhesive composition is based on a pressure sensitive adhesive composition according to the invention.

Salts and/or hydrocolloids, as absorbing particles or polymers, may be added to the composition to create an absorbing material.

Salt may be a water-soluble salt and can be inorganic salt or organic salt.

According to one embodiment of the invention, the adhesive composition comprises water soluble inorganic salt from the group of but not limited to NaCl, $CaCl_2$, $K_2SO_4$, $NaHCO_3$, $Na_2CO_3$, KCl, NaBr, NaI, $K_1$, $NH_4Cl$, $AlCl_3$ and mixtures thereof, preferably NaCl.

According to another embodiment of the invention, the adhesive composition comprises water soluble organic salt from the group of but not limited to $CH_3COONa$, $CH_3COOK$, COONa, COOK and mixtures thereof.

The adhesive can be used without particles in devices, which rely on transmission rather than absorption.

As with traditional HC adhesives, most liquid absorbing polymeric particles can be used, including microcolloids. A special advantage with a permeable adhesive is that a surface film will not block absorption completely.

More particularly, the hydrocolloids may be guar gum, locust bean gum (LBG), pectin, alginates, potato starch, gelatine, xanthan, gum karaya; cellulose derivatives (e.g. salts of carboxymethylcellulose such as sodiumcarboxymethylcellulose, methylcellulose, hydroxyethyl cellulose and hydroxypropylmethylcellulose), sodium starch glycolate, polyvinylalcohol and/or polyethylene glycol.

Microcolloid particles are well known in the art e.g. from International Patent Application No. WO 02/066087, which discloses adhesive compositions comprising microcolloid particles. The microcolloid particles may have a particle size of less than 20 microns.

The invention also relates to medical devices comprising a pressure sensitive adhesive composition as described above.

The medical device comprising an adhesive composition according to the invention may be an ostomy appliance, a dressing (including wound dressings), a wound drainage bandage, a skin protective bandage, a device for collecting urine, an orthose or a prosthese, e.g. a breast prothesis, a faecal management device, and electronic device such as a measuring instrument or a power source, such as a battery.

The medical device may also be a tape (e.g an elastic tape or film), or a dressing or a bandage, for securing a medical device, or a part of the medical device to the skin, or for sealing around a medical device attached to the skin.

The medical device may in its simplest construction be an adhesive construction comprising a layer of the pressure sensitive adhesive composition according to the invention and a backing layer.

The backing layer is suitably elastic (has a low modulus), enabling the adhesive construction to conform to the skin movement and provide comfort when using it.

In a preferred embodiment of the invention, the backing material has a structured surface to improve the adhesion between adhesive and the backing material. Particularly preferred are backing materials where the molted adhesive can penetrate and create mechanical interlocking with, for example Non Woven and non-woven film laminates.

The thickness of the backing layer used according to the invention is dependent on the type of backing used. For polymer films, such as polyurethane films, the overall thickness may be between 10 to 100 μm, preferably between 10 to 50 μm, most preferred about 30 μm.

In one embodiment of the invention, the backing layer is non-vapour permeable.

In another embodiment of the invention, the backing layer is water vapour permeable and has a moisture vapour transmission rate above 500 g/m²/24 h. In this case the adhesive construction of the invention may provide a good moisture transmission rate and is able to transport a large quantity of moisture through the construction and away from the skin. Both the chemical composition and physical construction of the adhesive layer and the chemical and physical construction of the backing layer affect the water vapour permeability. With regard to the physical construction, the backing layer may be continuous (no holes, perforations, indentations, no added particles or fibers affecting the water vapour permeability) or discontinuous (it has holes, perforations, indentations, added particles or fibers affecting the water vapor permeability).

The moisture vapour transmission rate of the backing layer is suitably above 500 g/m²/24 h, most preferably above 1000 g/m²/24 h, even more preferred above 3000 and most preferred above 10.000.

In another embodiment of the invention, a layered adhesive construct comprising a backing layer and at least one layer of a pressure sensitive adhesive composition according to the invention.

The adhesive according to the invention may be foamed into foamed adhesive in a number of ways, either chemically or mechanically.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilisation of low boiling materials or by a combination of these methods.

Any of the commercially known chemical blowing agents may be used. The chemical blowing agents is suitably non-toxic, skin friendly, and environmentally safe, both before and after decomposition.

The amount of chemical blowing agent to be added to the adhesive mixture may range from about 0.01% up to about 90% by weight, with a practical range including about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process.

Another method for creating a foamed adhesive of the invention is a method where a mechanical process is used to add a physical blowing agent, similar to whipping the adhesive mass into froth, thus creating a foamed structure. Many processes are possible including processes involving incorporation of air, nitrogen, carbon dioxide, or other gases or low boiling point volatile liquids during the manufacturing process for the adhesive.

For some medical devices it is important that the adhesive has high moisture vapour transmission rate, whereas the water absorption capacity is less important. This is the case with very thin dressings (e.g. for use on the face), wound dressings having an absorbent element or pad incorporated into the dressing, skin protective dressings used over skin where there are no cuts or wounds, etc.

For these uses, the adhesive preferably has a high moisture vapour transmission rate but does not necessary need to have a high absorption capacity. A certain water absorption capacity may function as a buffer in case of severe perspiration. However, a high water absorption capacity also makes the water resistance of the adhesive lower, e.g. during washing or showering. Absorption of exudates from a wound may be handled by a separate absorbent element and the moisture vapour transmission rate of the adhesive is therefore in many cases more important than water absorption capacity.

According to one embodiment, the invention therefore relates to a dressing such as very thin dressings for use on the face, wound dressings having an absorbent element or a pad incorporated into the dressing, or skin protective dressings used over skin where there are no cuts or wounds.

According to a further embodiment, the invention relates to a medical device as above, e.g. a thin adhesive dressing, wherein the thickness of the adhesive layer is between 50 and 250 μm where it is thickest. The adhesive layer may thus have varying thickens or it may have a uniform thickness selected from values between 50 and 250 μm.

A dressing of the invention may in a preferred embodiment comprise an absorbing pad for the uptake of body fluids, especially wound exudates, so as to enable the wound dressing to keep a constant moist environment over the wound site, and at the same time avoiding maceration of the skin surrounding the wound.

According to still another embodiment of the invention, the medical device is a wound dressing as described above comprising an absorbent pad and where the thickness of the adhesive layer is between 50 and 300 μm where it is thickest. The adhesive layer may thus have varying thickens or it may have a uniform thickness selected from values between 50 and 300 μm.

An absorbent pad may be situated at the surface of the adhesive layer for contacting the wound or skin or between the adhesive layer and a backing.

A suitable foam material for use as a pad material for a dressing of the invention is e.g. a polyethylene foam, a polyurethane foam, a polyalkylene oxide and/or polyalkylene oxide siloxane foam.

An absorbent pad may comprise hydrocolloids, super absorbents, or foams or natural or synthetic materials which have extensive capacity to absorb body fluids, especially wound exudates. The absorbent pad may comprise an exudate distributing material. This renders it possible to utilise the areas of absorbent layer not being located right above the wound as well as the wetted surface of the absorbent layer will be enlarged and thus the evaporation through the backing layer will be enhanced.

The absorbent pad may be in the form of one or more layers, e.g. a multilayer, comprising layers of different absorption properties in order to optimise the absorption capacity of the absorbent layer. The absorbent pad may be in the form of a matrix structure, e.g. with incorporated particles. When the absorbent pad comprises a material capable of distributing the absorbed exudate, full utilisation of the absorption capacity in the dressing may be obtained.

The absorbent pad may comprise particles or fibres of any absorbent material known per se being suitable for use in wound care devices, e.g. polyacrylate, CMC, cellulose or derivatives thereof, gums, foam or alginate. A dressing of the invention may be produced in a manner known per se for applying an adhesive material onto a backing, e.g. laminating or dye casting or spreading the adhesive to a part of or the whole of one surface of the backing.

A dressing of the invention is optionally covered partly or fully by one or more release liners, or cover films to be removed before or during application. A protective cover or release liner may for instance be siliconised paper. It does not need to have the same contour as the dressing, and a number of dressings may be attached to a larger sheet of protective cover. The release liner may be of any material known to be useful as a release liner for medical devices.

The protective cover is not present during the use of the dressing of the invention and is therefore not an essential part of the invention. Furthermore, the dressing of the invention may comprise one or more "non touch" grip (s) known per se for applying the dressing to the skin without touching the adhesive layer. Such a non-touch grip is not present after application of the dressing. For larger dressings it is suitable to have 2 or 3 or even 4 "non-touch" grips.

Dressings comprising an absorbing pad or element for the uptake of body fluids, especially wound exudates, so as to enable the wound dressing to keep a constant moist environment over the wound site, are described in WO 02/05737, U.S. Pat. No. 5,086,764, EP 641 553, WO 91/01706 and EP 236 104. The adhesive according to the present invention may replace the adhesive comprised in any of these known dressings.

Flexibility in the adhesive part of a medical device is often achieved by device design, such as bevelling or patterning in the adhesive.

A dressing or adhesive sheet of the invention may have bevelled edges in order to reduce the risk of "rolling-up" the edge of the dressing reducing the wear-time. A bevelling may be carried out discontinuously or continuously in a manner known per se e.g. as disclosed in EP Patent No. 0 264 299 or U.S. Pat. No. 5,133,821

In another aspect, the invention relates to a wafer for an ostomy appliance comprising an adhesive construction as described above.

An ostomy appliance of the invention may be in the form of a wafer forming part of a two-piece appliance or in the form of a one-piece appliance comprising a collecting bag for collecting the material emerging from the stoma. A separate collecting bag may be attached to the wafer by any manner known per se, e.g. through mechanical coupling using a coupling ring or through use of adhesive flanges.

A wafer for an ostomy appliance of the invention also typically comprises a water vapour permeable and water impervious reinforcement material and a release liner as discussed above.

An ostomy appliance of the invention may be produced in a manner known per se from materials conventionally used for the preparation of ostomy appliances.

Devices with advantageous properties may be obtained using the permeable adhesives of the invention in laminated constructions.

In one embodiment of the invention, the construction further comprises at least one layer of a water absorbing adhesive.

Devices with very good adhesion under extreme conditions, for example high moisture load from heavy sweating, may be obtained by placing a layer, preferably a thin layer, of permeable but non-absorbing adhesive (no hydrophilic fillers) of the invention between a water absorbing adhesive and the skin. This way, good adhesive power can be maintained even after the adhesive has absorbed a considerable amount of water.

It is a particular advantage to use the absorbing adhesive constructions according to the invention in connection with ostomy appliances, because the adhesive can be made resistant to the aggressive fluids from the stoma, without sacrificing too much water absorption. Hence, it is possible to make devices, which shield the skin efficiently from the corrosive stoma fluids, and at the same time provides a healthy non-occlusive microenvironment between the adhesive and the skin.

In a further embodiment, the invention relates to prosthesis of the type to be adhered to the skin of the user, such as a breast prosthesis comprising an adhesive construction according to the invention.

The invention also relates to a urine collecting device comprising an adhesive construction as described above.

Urine collecting devices according to the invention may be in the form of uri-sheaths.

As mentioned above, the medical device may also be a medical tape e.g. for securing a device or a part of a device to the skin.

The medical device according to the invention may also be a measuring instrument or a therapeutic instrument, which is attached to the skin, such as devices useful for measuring ECG (Electro CardioGraphy), EMG (Electro MyoGraphy), EEG (Electro EncephaloGraphy), blood glucose, pulse, blood pressure, pH, and oxygen.

Such measuring instruments are known in the art and they are usually attached to the skin by a pressure sensitive adhesive.

Examples of such devices are described in e.g. WO 03/065926, U.S. Pat. Nos. 5,054,488, 5,458,124, 6,372,951, 6,385,473 WO 99/59465 and US application No. 2003/0009097. An adhesive construction in accordance with the present invention may replace the adhesive constructions used for attaching these devices to the skin.

In another embodiment of the invention, the adhesive is part of a faecal-collecting device, attaching a bag or another collecting device to the perianal skin.

In one embodiment of the invention, the medical device is a beta-sterilised medical device.

EXPERIMENTAL

Laboratory Methods
Method 1: Mixing

The adhesives were compounded in a Brabender mixer from Brabender OHG, Duisburg, Germany (contains about 60 grams) or a Herrmann Linden LK II 0,5 from Linden Maschinenfabrik, Marienheiden, Germany (contains about 600 grams). The chamber temperature in the mixer was approx 120° C. and the adhesive was compounded with 50-60 rpm.

Premixtures were made from each polymer. The polymer was added to the mixer and the mixer was started. When the polymer was melted and had a smooth surface, oil was added slowly in small steps, starting with a few ml, followed by increasing amounts. The following part of oil was not added until the previous part was well mixed into the polymer.

For Levamelt/PPO adhesives, the ratio between Levamelt and PPO in the premixture was typically approx 1:1.

The adhesive was compounded from the premixtures of polymer and oil. The premixture was added to the mixer together with resin and/or high MFI polymer, if such was used in the formulation. The mixer was started, and when the polymer was melted and had a smooth surface, additional oil was added slowly in small steps, starting with a few ml, followed by increasing amounts.

If the formulation included hydrocolloids or salt, these were added to the adhesive and mixed for approx 15 min.

Method 2: Mechanical Degradation of Precrosslinked Levapren

In some cases, it was necessary to perform a mechanical degradation of the precrosslinked EVA, e.g. when Levapren VPKA 8857 was used. The polymer was mixed for about 10 hours in a cold Hermann Linden LK II 0,5 mixer to get mechanical break down of the polymer chains. It is important to notice that the heating system was not turned on and the mixing speed kept low, app. 20 rpm, to ensure optimal mechanical work on the polymer. The break down of the polymer was followed by visual inspection of a thermoformed film of the treated polymer. The mechanical treatment was continued until only a minor amount of polymer gel-lumps remained.

Method 3: Gamma Irradiation

Approx 1 kilo of the polymer was placed in a plastic bag. The bag was packed and sent to the gamma irradiation supplier, e.g. BGS Beta-Gamma Service, Wiehl, Germany. The polymer was irradiated with the specified gamma dose, e.g. 30 kGy. The gamma radiation increases the molar weight of the polymer. When the polymer was returned, it was mixed with oil, to obtain premixtures as described above.

Method 4: Determination of Moisture Vapour Transmission Rate (MVTR)

MVTR was measured in grams per square meter (g/m2) over a 24 hours period using an inverted cup method.

A container or cup that was water and water vapour impermeable having an opening was used. 20 ml saline water (0.9% NaCl in demineralised water) was placed in the container and the opening was sealed with the test adhesive film. The container was placed into an electrically heated humidity cabinet and the container or cup was placed up side down such that the water was in contact with the adhesive. The cabinet was maintained at 37° C. and 15% relative humidity (RH). The weight loss of the container was followed as a function of time. The weight loss was due to evaporation of water vapour transmitted through the adhesive film. This difference was used to calculate Moisture vapour transmission rate or MVTR. MVTR was calculated as the weight loss pr time divided by the area of the opening in the cup (g/m$^2$/24 h). The MVTR of a material was a linear function of the thickness of the material. Thus, when reporting MVTR to characterise a material, it was important to inform the thickness of the material which MVTR was reported. We used 150 μm as a reference. If thinner or thicker samples were measured, the MVTR was reported as corresponding to a 150 μm sample. Thus a 300 μm sample with a measured MVTR of 10 g/m$^2$/24 h was reported as having MVTR=20 g/m$^2$/24 h for a 150 μm sample because of the linear connection between thickness of sample and MVTR of sample.

Finally, we noted that by using this method, we introduced an error by using a supporting PU film. Utilising the fact, that the adhesive/film laminate was a system of two resistances in series eliminated the error. When the film and the adhesive were homogeneous, the transmission rate may be expressed as:

$$1/P(\text{measured})=1/P(\text{Film})+1/P(\text{Adhesive})$$

Hence by knowing the film permeability and thickness of the adhesive, it was possible to calculate the true permeability of the adhesive (P(Adhesive)) using the following expression:

$$P(\text{adhesive})=d(\text{Adhesive})/150\text{micron}*1/(1/P(\text{measured})-1/P(\text{Film}))$$

where d(Adhesive) was the actual measured thickness of the adhesive and P(Film) was the MVTR of the film without any adhesive on and P(measured) was the actual measured MVTR.

Method 5: Determination of Peel Failure Mode:

Peel failure mode was determined by peeling a suitable sample from skin.

Peel failure mode, i.e. adhesive or cohesive failure of the adhesive, was visually observed. Cohesive failure was unwanted, as adhesives with cohesive failure were likely to leave residues on the substrate when removed.

The test samples were prepared by thermoforming an approximately 200 micron adhesive film between two release liners. Said adhesive film was transfer coated onto an 80 gsm elastic non-woven from BBA Fiberweb (Dreamex, CS9540002, 80 gsm), and heat treated at 100° C. for about 5 minutes to thoroughly bond the adhesive to the NW. 1 cm wide test specimens were cut along the low module axis of the non-woven.

The test specimens were applied to the underside of the forearm and left for about 2 hours before they were peeled. The results were reported as Adhesive or Cohesive peel failure mode.

Method 6: DMA and Determination of G' and Tan(δ)

The parameters G' and tan(δ) were measured as follows: The adhesives were pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurements were carried out at 32° C.

Materials

| Name | Chemistry | Supplier |
| --- | --- | --- |
| Levamelt | Copolymers of ethylene and vinyl acetate (VA). | Lanxess, Germany |
| Evatane | Copolymers of ethylene and vinyl acetate (VA). | ATOFINA Chemicals Inc. |
| Polyglycol B01/120 (PPO) | Poly(propylene oxide) oil (Mw = 2000) | Clariant, Germany |
| Pine Crystal, KE311 resin | Hydrogenated rosin ester | Arakawa, Japan |
| Suprasel, NaCl | Fine particulate Sodium Chloride powder | Akzo Nobel Salt A/S |
| Aquasorb A800 | Crosslinked CMC particles | Hercules |
| Bioflex 130 | PU film, 25 micron | Scapa |
| Dreamex CS9540002 | PU/PE NW, 80 gsm | BBA Fiberweb |

Results

EXAMPLE 1

Permeability Of Different EVA Polymers

Film was prepared by thermoforming the neat polymer in a warm press at about 100° C., and MVTR was measured (Method 4):

| EVA polymer permeability | | MVTR measured | MVTR 150 micron |
|---|---|---|---|
| Sample name | Support Film | g/m$^2$/24 hours | g/m$^2$/24 hours |
| LDPE, 160 micron | non | 15 | 16 |
| Evatane 28-25, 270my | | 65 | 117 |
| Levamelt 400 (40% VA, 290 micron) | non | 47 | 110 |
| Levamelt 450 (45% VA, 290 micron) | non | 94 | 181 |
| Levamelt 500 (50% VA, 270 micron) | non | 111 | 201 |
| Levamelt VPKA 8857 (50% VA, 340 micron) | non | 125 | 280 |
| Levamelt 700 (70% VA, 330 micron) | non | 118 | 240 |

EVA polymers with low VA have a low MVTR and hence make less suitable base polymers for a permeable hot-melt processable pressure sensitive adhesive. In addition only fairly hydrophobic oil and resins are compatible with low VA EVA, and hence the resulting adhesives will have a low permeability.

EXAMPLE 2

Peel and Permeability of Different Adhesives Based on Eva Polymers With Different MFI Index The following adhesives were hot-melt compounded according to methods 1, 2 and 3. Peel failure mode was determined according to method 5:

| | STR041.1 | STR040.7 | STR041.2 | STR040.8 | STR041.3 | STR037.4 |
|---|---|---|---|---|---|---|
| Levamelt 700 MFI = 4 | 45.0 | | | | | |
| Levamelt 700, 30KGy, MFI < 2 | | 45.0 | | | | |
| Levamelt 500 MFI = 3 | | | 28.6 | | | |
| Levamelt 500, 50 KGy, (Levapren VPKA 8857) MFI < 2 | | | | 28.6 | | |
| Levamelt 450 MFI = 5 | | | | | 25.0 | |
| Levamelt 450, 30 KGy, MFI < 2 | | | | | | 25.0 |
| Levamelt VP KA 8896 (MFI >> 2) | | | 19.0 | 19.0 | 10.0 | 10.0 |
| PolyGlycol PPO B01/120 | 55.0 | 55.0 | 52.4 | 52.4 | 65.0 | 65.0 |
| Peel failure mode | Cohesive | Adhesive | Cohesive | Adhesive | Cohesive | Adhesive |

The example illustrates that adhesives made with polymers with MFI<2 have a much improved ratio between adhesiveness and cohesive strength, i.e. they leave little or no residues on the substrate when peeled. Adhesives made only with polymers with MFI>2 have a tendency to fail cohesively and hence leave an unacceptable amount of residues when removed.

EXAMPLE 3

Permeability of Adhesives with High and Low Resin Content

Four adhesives were compounded according to the methods 1, 2 and 3

| | STR040.7 | STR043.1 | STR043.2 | STR043.3 |
|---|---|---|---|---|
| Levamelt 700, 30 KGy | 45.0 | 45.0 | 45.0 | 45.0 |
| Polyglycol PPO B01/120 | 55.0 | | 45.0 | 27.5 |
| Pine Crystal KE-311 | | 55.0 | 10.0 | 27.5 |

The adhesives were thermoformed to about 250 microns between a PU film (Bioflex 130) and a release liner. The transmission rate was measured according to Method 4:

| | Resin % | Transmission g/m$^2$/day |
|---|---|---|
| STR040.07 | 0 | 1127 |
| STR043.02 | 10 | 703 |
| STR043.03 | 32.5 | 350 |
| STR043.01 | 55 | 37 |

The example shows that an adhesive according to the invention may contain some tackifier resin, but that they generally reduce transmission. Levels below about 50% seem to be acceptable, but preferably the level should be even lower.

EXAMPLE 4

Adhesives According to the Invention

The table beneath shows examples of adhesive compositions prepared according to the invention and methods 1, 2 and 3.

|  | Sample number | | | | | |
| --- | --- | --- | --- | --- | --- | --- |
|  | STR039.4 | STR039.11 | STR039.L9 | STR034.25 | STR040.7 | STR005.42 |
| Levamelt VPKA 8857 MFI < 2 | 25% | 27% | Laminate of Film + 800 micron STR039.4 + 100 micron STR039.11 | 25% |  | 30% |
| Levamelt 700, 30KGy Gamma MFI < 2 |  |  |  |  | 45% |  |
| Levamelt 700 MFI = 4 | — | — |  | 5% |  | — |
| Levamelt VP KA 8896 MFI >> 2 | 20% | 13.5% |  | 5% |  |  |
| PolyGlycol B01/120 | 55% | 49.5% |  | 65% | 55% | 50% |
| Pine Crystal, KE-311 | — | — |  | — |  | 20% |
| Suprasel, NaCl | — | 10% |  | — |  | — |
| Peel failure mode | adhesive | adhesive | adhesive | adhesive | adhesive | adhesive |
| Transmission (150 micron) | 820 g/m2/day | 2990 g/m2/day | nm | 1210 g/m2/day | 1130 g/m2/day | 490 g/m2/day |
| Module, G', 1 Hz | 21000 Pa | 40400 Pa | nm | 13800 Pa | 30500 Pa | 21400 Pa |

It can be noted that key performance properties, such as peel failure mode, transmission and moduli, all comply well with the criteria for an adhesive according to the invention.

EXAMPLE 5

Sterilisation Tolerance

Materials:

| Name | Chemistry | Supplier |
| --- | --- | --- |
| Levamelt | Copolymers of ethylene and vinyl acetate (VA). Grades with VA content between 40% and 80% | Lanxess, Germany |
| B01/120 (PPO) | Poly(propylene oxide) oil (Mw = 2000) | Clariant, Germany |
| Pine Crystal KE311 | Hydrogenated rosin ester | Arakawa, Japan |
| Citrofol BII | Acetyl tributyl citrate | Jundbunzlauer, Germany |
| Blanose | carboxy-methyl-cellulose (CMC) hydrocolloid | Aqualon/Hercules |
| Aquasorb A800 | x-linked CMC hydrocolloid | Aqualon/Hercules |

Adhesives:

|  | STR020.03 | STR025.F03 | STR025.14 | STR025.15 |
| --- | --- | --- | --- | --- |
| Levamelt 400 | 16.9 | 19.4 |  |  |
| Levamelt 700 | 20.0 | 9.7 |  |  |
| PPO B01/120 | 27.0 | 29.1 |  |  |
| KE311 resin | 36.0 | 38.8 |  |  |
| Citrofol BII |  | 3.0 |  |  |
| Blanose |  |  | 20.0 |  |
| Aquasorb A800 |  |  |  | 20.0 |
| STR025.F03 |  |  | 80.0 | 80.0 |

The adhesives were produced according to method 1, thermoformed into 1 mm sheets which were sent for Beta-ray sterilisation at a dose of 0, 17.5 KGy & 2×17.5 KGy. DMA was performed according to method 6.

Results:

| Sample No. | Dose (*17.5kGy) | G' (Pa) at 1 Hz & 32° C. | tan(δ) at 1 Hz & 32° C. | G' (Pa) at 0.01 Hz & 32° C. | tan(δ) at 0.01 Hz & 32° C. |
| --- | --- | --- | --- | --- | --- |
| STR020.03 | 0 | 38900 | 0.59 | 5700 | 0.83 |
|  | 1* | 37700 | 0.60 | 5270 | 0.86 |
|  | 2* | 33600 | 0.60 | 5160 | 0.78 |
| STR025.F03 | 0 | 23100 | 0.50 | 8410 | 0.26 |
|  | 1* | 22900 | 0.50 | 8440 | 0.26 |
|  | 2* | 24500 | 0.50 | 8910 | 0.25 |
| STR025.14 | 0 | 43000 | 0.49 | 16600 | 0.26 |
|  | 1* | 46500 | 0.49 | 18500 | 0.26 |
|  | 2* | 41400 | 0.50 | 15100 | 0.27 |
| STR025.15 | 0 | 50000 | 0.51 | 18700 | 0.30 |
|  | 1* | 43100 | 0.50 | 16200 | 0.28 |
|  | 2* | 42100 | 0.53 | 14600 | 0.30 |

The results show that Beta-sterilisation introduce no or only very slight changes in mechanical properties; G' and tan(δ) are constant, within experimental error, i.e. no significant cross linking or breakdown of the polymer backbone is introduced.

The invention claimed is:
1. A layered adhesive construct comprising a backing layer and at least one layer of a pressure sensitive, hot melt processable adhesive composition comprising polypropyleneoxide in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10min (190° C/21.1 N), wherein the at least one polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate monoxide, and combinations thereof,
provided that when the polar polyethylene copolymer is ethylene vinyl acetate, the ethylene vinyl acetate has a content of at least 40% (w/w) vinyl acetate.
2. The layered adhesive construct according to claim 1, wherein the final adhesive in continuous form exhibits a moisture vapour transmission rate of at least 100 g/m²/day for a 150 m adhesive sheet when measured according to MVTR Test Method.

3. The layered adhesive construct according to claim 1, wherein the polar polyethylene copolymer is ethylene vinyl acetate.

4. The layered adhesive construct according to claim 3, wherein the ethylene vinyl acetate has a content of 40-80% (w/w) vinyl acetate.

5. The layered adhesive construct according to claim 1, wherein the content of the polar polyethylene copolymer is 10-45% (w/w) of the final adhesive.

6. The layered adhesive construct according to claim 1, wherein the polar polyethylene copolymer has a molecular weight of above 250,000 g/mol.

7. The layered adhesive construct according to claim 1, wherein the composition further includes an additional plasticizer selected from the group consisting of of liquid rosin derivatives, aromatic olefin oligomers, vegetable and animal oils and derivatives, esters, ethers and glycols, and alpha-butoxy-polyoxypropylene.

8. The layered adhesive construct according to claim 7, wherein the content of the polypropylene oxide plus the additional plasticizer is 20-70% (w/w) of the final adhesive.

9. The layered adhesive construct according to claim 1, wherein the composition further comprises a polymer with MFI >2(190° C/21.1N).

10. The layered adhesive construct according to claim 1, wherein the composition further comprises a tackifying resin.

11. The layered adhesive construct according to claim 10, wherein the content of the tackifying resin is 0.1-40% (w/w) of the final adhesive.

12. The layered adhesive construct according to claim 1, wherein the composition further comprises an additional plasticiser selected from the group consisting of mineral oil, citrate oil, paraffin oil, phatalic acid esters, adepic acid esters, and liquid and solid resin.

13. The layered adhesive construct according to claim 1, wherein the composition further comprises a polyethylene wax.

14. The layered adhesive construct according to claim 1, wherein the composition further comprises other ingredients selected from the group consisting of antioxidants, stabilisers, fillers, pigments, flow modifiers, and active ingredients.

15. The layered adhesive construct according to claim 14, wherein the other ingredients are polar active ingredients.

16. The layered adhesive construct according to claim 1, wherein the composition further comprises absorbing particles.

17. The layered adhesive construct according to claim 16, wherein the absorbing particles comprise hydrocolloid and the amount of hydrocolloid is below 50% w/w of the total composition.

18. The layered adhesive construct according to claim 1, wherein the composition further comprises a salt.

19. The layered adhesive construct according to claim 18, wherein the salt is a water soluble inorganic salt selected from the group consisting of $NaCl$, $CaCl_2$, $K_2SO_4$, $NaHCO_3$, $Na_2CO_3$, $KCl$, $NaBr$, $NaI$, $KI$, $NH_4Cl$, $AlCl_3$, and mixtures thereof.

20. The layered adhesive construct according to claim 18, wherein the salt is a water soluble organic salt selected from the group consisting of $CH_3COONa$, $CH_3COOK$, $HCOONa$, $HCOOK$ and mixtures thereof.

21. A beta-sterilised layered adhesive construct according to claim 1.

22. The layered adhesive construct according to claim 1, wherein the construct further comprises at least one layer of a water absorbing adhesive.

23. The layered adhesive construct according to claim 22, wherein the layer of a pressure sensitive adhesive composition is between said layer of a water absorbing adhesive and the skin.

24. A medical device comprising (a) a pressure sensitive hot melt processible adhesive composition containing polypropyleneoxide in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10min (190° C/21.1N), wherein the at least one polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate monoxide, and combinations thereof, and (b) a backing layer.

25. The medical device according to claim 24, wherein the backing layer is non-vapour permeable.

26. The medical device according to claim 24, wherein the backing layer is water vapour permeable and has a moisture vapour transmission rate above 500 g/m²/24h.

27. The medical device according to claim 24, wherein the medical device is a dressing, an ostomy appliance, a prosthesis, a breast prosthesis, a urine collecting device, a faecal management device, a measuring instrument or a therapeutic instrument, a medical tape, or a dressing or bandage for sealing around a medical device on the skin.

28. The medical device according to claim 24, wherein the medical device is a beta-sterilised medical device.

29. The layered adhesive construct according to claim 1, wherein the content of the polar polyethylene copolymer is 15-30% (w/w) of the final adhesive.

30. The layered adhesive construct according to claim 7, wherein the content of the polypropylene oxide plus the additional plasticizer is 40-60% (w/w) of the final adhesive.

31. The layered adhesive construct according to claim 10, wherein the tackifying resin is selected from the group consisting of natural, modified and synthetic resins, polar resins, rosin esters and derivatives thereof, and pure aromatic monomer resins.

32. The layered adhesive construct according to claim 10, wherein the content of the tackifying resin is 10-20% (w/w) of the final adhesive.

* * * * *

UNITED STATES PATENT AND TRADEMARK OFFICE
CERTIFICATE OF CORRECTION

PATENT NO.         : 8,710,130 B2                                  Page 1 of 1
APPLICATION NO.    : 12/452513
DATED              : April 29, 2014
INVENTOR(S)        : Lykke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this

Twenty-ninth Day of September, 2015

Michelle K. Lee
*Director of the United States Patent and Trademark Office*